United States Patent [19]

Champseix et al.

[11] 4,237,139

[45] Dec. 2, 1980

[54] 4-(3-(4-QUINOLYL)PROPYL)PIPERIDINES, THEIR PREPARATION AND THEIR USE AS MEDICINES

[75] Inventors: Alain A. Champseix, Forges les Bains; Claude G. A. Gueremy, Houilles; Gerard R. Le Fur, Villeneuve la Garenne, all of France

[73] Assignee: Pharmindustrie, Gennevilliers, France

[21] Appl. No.: 968,718

[22] Filed: Dec. 12, 1978

Related U.S. Application Data

[63] Continuation-in-part of Ser. No. 806,418, Jun. 14, 1977, abandoned.

[30] Foreign Application Priority Data

Jun. 18, 1976 [FR] France .............................. 76 18555
Aug. 3, 1978 [FR] France .............................. 78 22968

[51] Int. Cl.³ .................... A61K 31/47; C07D 211/32; C07D 401/06
[52] U.S. Cl. .................................. 424/258; 546/153; 546/156; 546/184
[58] Field of Search ................ 424/258; 546/153, 156, 546/184

[56] References Cited

PUBLICATIONS

Popli et al., J. Sci. Ind. Res. Sect. c19, 298–302 (1960).
P. Rabe, Ber. 55, 532 (1922).
V. Prelog et Coll., Ber. Der Deutschen Chemischen Gesellschaft, 72B, 1325–1333 (1939).

*Primary Examiner*—Stanley J. Friedman
*Attorney, Agent, or Firm*—Beveridge, DeGrandi, Kline & Lunsford

[57] ABSTRACT

Pharmaceutical preparations containing as active ingredient a compound having the formula:

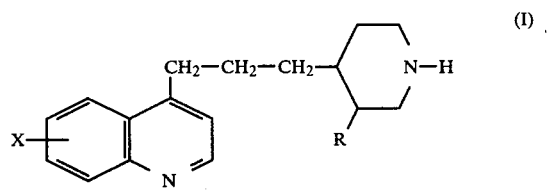

wherein R represents hydrogen, alkyl having 1 to 4 carbon atoms or alkenyl having 2 to 4 carbon atoms; and X represents hydrogen, alkyl, alkoxy or alkylthio, the alkyl groups of each containing 1 to 4 carbon atoms, halogen (chlorine, fluorine, bromine or iodine), trifluoromethyl, nitro, hydroxy, amino or amino substituted by one or two alkyl groups or by acyl or alkylsulphonyl, the alkyl groups of each containing 1 to 4 carbon atoms, which are particularly advantageous for the treatment of pathological states caused by a disturbance in the functioning of the serotoninergical systems in mammals. These preparations may also be used as anxiolytics.

15 Claims, No Drawings

4-(3-(4-QUINOLYL)PROPYL)PIPERIDINES, THEIR PREPARATION AND THEIR USE AS MEDICINES

This application is a continuation-in-part of application Ser. No. 806,418 filed June 14, 1977 and now abandoned.

The present invention relates to new medicaments (pharmaceutical preparations) based on quinoline derivatives which are particularly advantageous for the treatment of pathological states caused by a disturbance in the functioning of the serotoninergical systems in mammals. In particular, these medicaments may be used as psychotropic medicines, and more particularly as antidepressants and as medicaments which help to make sleep regular. They also have interesting activities on the cardiovascular system and can be used on that basis more particularly as antiarythmic medicaments and as regulators of the vasoconstriction of blood vessels, especially in the treatment of migraines. They may also be used as anxiolytics.

These medicaments contain as active ingredient a compound having the formula:

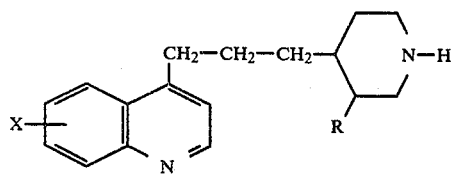

wherein R represents hydrogen, alkyl having 1 to 4 carbon atoms or alkenyl having 2 to 4 carbon atoms; and X represents hydrogen, alkyl, alkoxy or alkylthio, the alkyl groups of each containing 1 to 4 carbon atoms, halogen (chlorine, fluorine, bromine or iodine), trifluoromethyl, nitro, hydroxy, amino or amino substituted by one or two alkyl groups or by acyl or alkylsulphonyl, the alkyl groups of each containing 1 to 4 carbon atoms, or a pharmaceutically acceptable salt thereof, i.e., a salt of said compound with a pharmaceutically acceptable acid. Preferably the compounds are present in a pharmaceutically acceptable carrier therefor.

Preferably the medicaments according to the present invention contain as active ingredient a compound of formula (I) wherein R represents hydrogen, vinyl or ethyl and X represents hydrogen or methoxy in position 6, or a pharmaceutically acceptable salt thereof.

Some of the compounds of formula (I) are already known. These known compounds correspond to the following cases (see V. Prelog et Coll., Berichte der Deutschen Chemischen Gesellschaft, 72B, 1325-1333, 1939; and S. P. Popli et M. L. Dhar, J. Sci. Ind. Res., Sect. C 19, 298-302, 1960):

R and X represent hydrogen; and

R represents vinyl or ethyl and X represents hydrogen or methoxy in position 6, the carbon atom bearing the R group and the carbon atom in position 4 on the piperidine ring both having the rectus (R) configuration.

However, none of these known compounds has been known or suggested until now as a medicament, although the compound wherein R represents CH=CH₂ and X represents OCH₃ in position 6 showed an antiamoebic activity in the experimental amoebiasis of rats (cf. Popli and Dhar, supra).

The compounds of the formula:

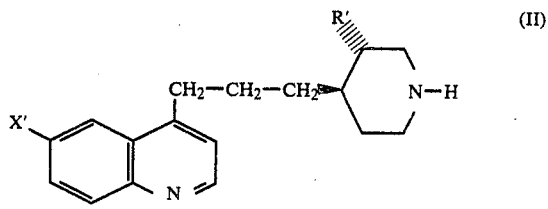

wherein X' is hydrogen or methoxy, R' is vinyl or ethyl, the carbon atom bearing the R' group has the sinister (S) configuration and the carbon atom bearing the 3-(4-quinolyl)propyl group, that is to say the carbon atom in position 4 on the piperidine ring, has the rectus (R) configuration, are new compounds and as such form a part of the present invention.

The compounds of formula (I) may be prepared by reducing products of formula (III):

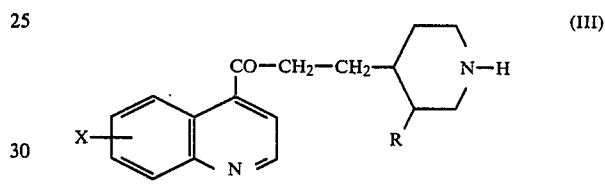

wherein X and R have the same definitions as in formula (I).

For this reduction, methods, known per se, are used which enable the CO group to be converted into a CH₂ group, for example those methods described by R. B. Wagner and H. D. Zook, SYNTHETIC ORGANIC CHEMISTRY, p. 5, J. Wiley & Sons, 1953, which is relied on herein for this purpose and the disclosure thereof incorporated herein by reference. Hydrazine hydrate is advantageously used as the reducing agent in the presence of an alkali metal hydroxide such as sodium hydroxide in a solvent such as an alcohol.

One variant for the preparation of the products of formula (I), wherein R represents alkyl, comprises catalytically hydrogenating the corresponding products of formula (I) wherein R represents alkenyl. This hydrogenation may be effected, for example, at ambient temperature, under a pressure of hydrogen equal to atmospheric pressure, in an inert solvent such as an alcohol (for example methanol or ethanol) or an acid (for example acetic acid), in the presence of a catalyst such as palladium, nickel, rhodium, ruthenium or platinum.

The compounds of formula (II) wherein R' is vinyl may also be prepared by heating in an acid medium compounds of the formula:

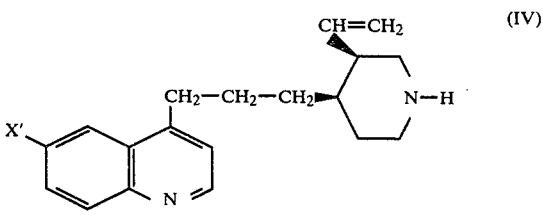

wherein the carbon atom bearing the vinyl group and the carbon atom in position 4 on the piperidine ring both have the rectus (R) configuration.

Once the reaction has terminated, the reaction mixture obtained in the above processes is treated according to conventional physical methods (evaporation, extraction by means of a solvent, distillation, crystallization, chromatography, etc.) or conventional chemical methods (formation of a salt and regeneration of the base, etc.) so as to isolate the product of formula (I) in a pure state, either in the form of the free base or in the form of a salt of this free base with an acid.

The compounds of formula (I) in the form of the free base may, if desired, be converted into pharmaceutically acceptable addition salts with a mineral or organic acid by the action of such an acid in a suitable solvent.

A certain number of products of formula (III) are already known. For example, the product of formula (III) wherein R and X are hydrogen atoms has been prepared by P. Rabe as described in Ber., 55, 532, 1922, which is relied on herein for this purpose and the disclosure incorporated by reference, by condensing the ethyl ester or quinoline 4-carboxylic acid of formula (V) with the ethyl ester of β-(N-benzoyl-4-piperidyl)propionic acid of formula (VI) and hydrolyzing the obtained β-keto ester of formula (VII), according to the following reaction diagram:

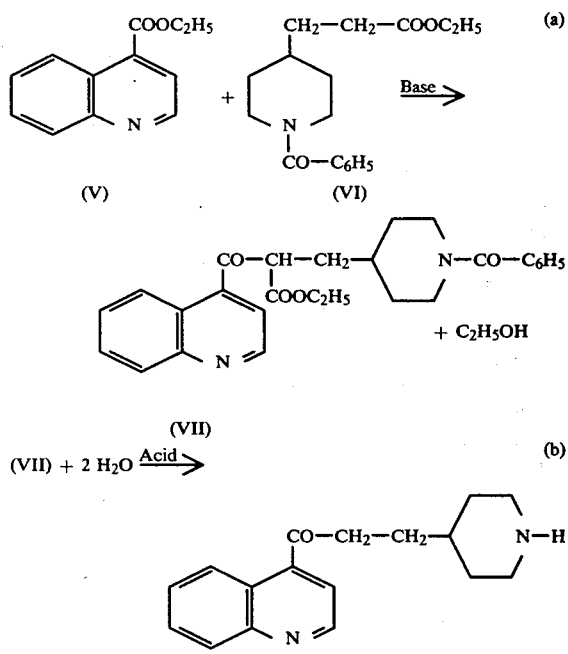

This method was later used, in principle, for the preparation of products of formula (III) wherein R represents $CH=CH_2$ or $C_2H_5$, and X represents H, OH, $OCH_3$, $CF_3$, alkyl or halogen according to U.S. Pat. Nos. 3,753,992; 3,857,846; and 3,869,461 which are relied on herein and the disclosures thereof incorporated herein by reference, and it may be extended to the synthesis of all the derivatives of formula (III). It is sufficient therefor to replace in reaction (a) set out above the ester of formula (V) by an ester of formula (VIII) wherein X has the same definitions as in formula (I), and the ester of formula (VI) by an ester of formula (IX) wherein R has the same definitions as in formula (I):

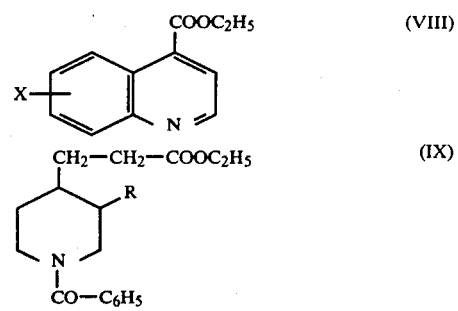

The execution of the condensation reactions of type (a) and the hydrolysis reactions of type (b) utilize processes known per se as taught, respectively, in THE ACETOACETIC ACID ESTER CONDENSATION, C. R. Hauser and Coll., *Organic Reactions*, Vol. 1, P. 266, Wiley & Sons, 1942, and CLEAVAGE OF β-KETOESTERS, R. B. Wagner & H. D. Zook, *Synthetic Organic Chemistry*, P. 327, Wiley & Sons, 1953, which are relied on herein for this purpose and the disclosures incorporated by reference.

In the particular case wherein R represents $CH=CH_2$ or $C_2H_5$ and X represents H or $OCH_3$ in position 6, the starting products of formula (III) may be prepared advantageously by rearranging in an acid medium the major cinchona alkaloids and the corresponding hydrobases or their stereomers as described by S. W. Pelletier, CHEMISTRY OF THE ALKALOIDS, p. 313, Reinhold, 1969, which is relied on herein and the disclosure incorporated by reference. Thus, the quinicine (compound of formula III wherein R represents $CH=CH_2$ and X represents $OCH_3$ in position 6) is obtained from quinine or quinidine, and cinchonicine (compound of formula III wherein R represents $CH=CH_2$ and X represents H) is obtained from cinchonine or cinchonidine.

The compounds of formula (I) have the property of inhibiting the uptake of serotonine by the membranes of cerebral neurons. They also have the property of causing the release of the serotonine contained either in the neurons or in the blood platelets. Either the property of inhibiting the uptake of serotonine or the property of causing the release of serotonine is predominant, depending on the nature of the R group and the configuration of the carbon atom which bears it.

For the compounds of formula (II), the property of causing the release of serotonine is much more pronounced than the property of inhibiting the uptake of this amine. Such a fact could result in a very rapid action at the time of treatment of depressive states (in this case the product acts on the serotonine of cerebral neurons) and of migraines (in this case the product acts on the serotonine of blood platelets).

The anxiolytic activity of benzodiazepines is well known. The presence of specific benzodiazepine receptors in membranes from the rat brain is also well established (cf, SQUIRES, R. F. et al., Nature 266 (1977), 732). There is a highly significant correlation between the activities of various benzodiazepines in pharmacological tests predictive of anxiolytic activity in mammals on the one hand and their affinities for the benzodiazepine receptors in the rat brain on the other hand. This affinity is measured by the capacity for displacing tritiated diazepam ($^3$H-diazepam) from its binding sites and is expressed by $K_i$ values in micromoles, which are calculated by using the equation:

$$K_i = IC_{50}[(1+C)K_D]$$

wherein:
 C = the concentration of $^3$H-diazepam
 $K_D$ = the affinity constant = 2.74 μM, and
 $IC_{50}$ = the concentration causing 50% inhibition of $^3$H-diazepam binding.

Up to now the affinity for the benzodiazepine receptors in rat brain has been shown to be a property possessed only by the benzodiazepines. In fact no other compound having an action on the central nervous system proved capable of displacing $^3$H-diazepam from its binding sites in a significant manner. For example, BRAESTRUP and SQUIRES in the European Journal of Pharmacology, 48 (1978) 263–267 disclose that they tested more than 100 compounds other than benzodiazepines and did not find any of them with significant affinity for the $^3$H-diazepam binding sites.

It has surprisingly been found that the compounds of formula (I), which are structurally different from benzodiazepines, are strongly active as $^3$H-diazepam displacers.

The properties of the compounds of formula (I) (specific action on the uptake and the release of serotonine and affinity for the benzodiazepine receptors in brain) confer to these compounds an original spectrum of activities. They are not only antidepressants, but also anxiolytics.

The following examples illustrate the invention without limiting it. In the examples, all parts are parts by weight unless otherwise specified.

EXAMPLE 1

4(R)-[3-(6-methoxy 4-quinolyl)propyl] 3(R)-vinyl piperidine.

18 grams of sodium hydroxide in pellet form were added to a suspension of 48 grams of quinicine in 200 ml. of diethyleneglycol and 23 grams of an 85% aqueous solution of hydrazine hydrate. Heating was effected slowly and when the temperature of 110° C., was reached, the medium was homogeneous. Heating was then effected for 1 hour at 130° C., then for 2 hours at 150° C. until the liberation of nitrogen ceased.

The reaction medium was thrown into 1 l. of ice-cold water. An oil salted out which was extracted by 500 ml. of ether. The organic phase was decanted, washed, dried on magnesium sulphate and then evaporated. An oil was obtained which was treated, in isopropanol medium (150 ml.), by hydrochloric acid. Thus, 20.5 grams of 4(R)-[3-(6-methoxy 4-quinolyl)propyl] 3(R)-vinyl piperidine dichlorohydrate, which melts at 175° C.–180° C., were obtained.

| Analysis for $C_{20}H_{26}N_2O$ . 2 HCl | | | |
|---|---|---|---|
| | C | H | N |
| Calculated: | 62.8 | 7.31 | 7.31 |
| Found: | 62.5 | 7.21 | 7.45. |

EXAMPLE 2

4(R)-[3-(4-quinolyl)propyl] 3(R)-vinyl piperidine.

Example 1 was repeated using 44.6 grams cinchonicine in place of the quinicine and 4(R)-[3-(4-quinolyl)propyl] 3(R)-vinyl piperidine was obtained in the form of its dichlorohydrate which melts at 189°–191° C.

| Analysis for $C_{19}H_{24}N_2$ . 2 HCl | | | |
|---|---|---|---|
| | C | H | N |
| Calculated: | 64.55 | 7.37 | 7.94 |
| Found: | 64.0 | 7.34 | 7.63. |

EXAMPLE 3

4(R)-[3-(6-methoxy 4-quinolyl)propyl] 3(R)-ethyl piperidine.

A well-stirred suspension containing 5.5 grams of 4(R)-[3-(6-methoxy 4-quinolyl)propyl]3(R)-vinyl piperidine dichlorohydrate in solution in 100 ml. of absolute ethanol and 1.5 grams of 10% palladium palladized carbon was maintained at ambient temperature under a pressure of hydrogen corresponding to an excess pressure of 50 mm of water relative to atmospheric pressure, until the absorption of the gas ceased.

The palladium was separated by filtration and then the alcoholic solution was concentrated. 5.5 grams of a raw product were obtained which, after recrystallization in 20 ml. of a 1/1 mixture of ethanol and isopropyl ether, provided 4.4 grams of 4(R)-[3-(6-methoxy 4-quinolyl)propyl] 3(R)-ethyl piperidine in the form of the dichlorohydrate which melts at 200° C.

| Analysis for $C_{20}H_{28}N_2O$ . 2 HCl | | | |
|---|---|---|---|
| | C | H | N |
| Calculated: | 62.3 | 7.8 | 7.28 |
| Found: | 62.05 | 8.04 | 7.10. |

EXAMPLE 4

4-[3-(4-quinolyl)propyl]piperidine.

A solution of 24 grams of 1-(4-quinolyl)-3-(4-piperidyl)-1-propanone (prepared according to P. Rabe's method, Ber., 55 532, 1922), 85 ml. of diethyleneglycol and 13.5 grams of an 85% aqueous solution of hydrazine hydrate was heated for 1 hour at 130° C. 31 grams of potassium hydroxide in pellet form were added, portion by portion, to the homogeneous solution obtained, then heating was effected for 4 hours at 140° C. until the liberation of gas ceased. The reaction medium was thrown into 500 ml. of ice-cold water, then extracted 3 times by 100 ml. of chloroform. The organic phase was decanted, washed, dried on potassium carbonate, and then evaporated. 23 grams of raw product were obtained, which product was treated by hydrochloric acid in isopropanol medium to form the dichlorohydrate. The latter, after recrystallization in a 1/1 ethanol-ether mixture, melts at 170° C.

| Analysis for $C_{17}H_{22}N_2$ . 2 HCl | | | |
|---|---|---|---|
| | C | H | N |
| Calculated: | 62.8 | 7.35 | 8.57 |
| Found: | 61.8 | 7.45 | 8.46. |

EXAMPLE 5

4(R)-[3-(4-quinolyl)propyl] 3(R)-ethyl piperidine.

A well-stirred suspension containing 40 grams of 4(R)-[3-(4-quinolyl)propyl] 3(R)-vinyl piperidine, 300 ml. of ethanol, 30 ml. of 37% hydrochloric acid and 15 grams of 10% palladium palladized carbon was contacted with hydrogen at 20° C. and atmospheric pressure. The absorption of hydrogen was very rapid and reached 2,400 ml. in an hour, said amount remaining steady thereafter. The solution was separated by filtration from the palladized carbon, then evaporated to dryness. The residue was taken up with 20 ml. of water made alkaline with 35 ml. of a 10 N solution of sodium hydroxide. The medium was extracted by 200 ml. of chloroform. The organic phase was dried on potassium carbonate, filtered then evaporated. The residue was treated with fumaric acid in ethanol medium.

Thus, 20 grams of 4(R)-[3-(4-quinolyl)propyl] 3(R)-ethyl piperidine fumarate, which melts at 143° C., were obtained.

| Analysis for 2 $C_{19}H_{26}N_2 \cdot 3\ C_4H_4O_4$ | | | |
|---|---|---|---|
|  | C | H | N |
| Calculated: | 65.7 | 7.02 | 6.13 |
| Found: | 65.28 | 7.14 | 6.47. |

EXAMPLE 6

4-[3-(6-butyl 4-quinolyl)propyl]piperidine

Example 1 was repeated using 3 grams of 1-(6-butyl 4-quinolyl)-3-(4-piperidyl)-1-propanone, which had been prepared according to the method of P. Rabe, Ber. 55, 532, 1922, in place of the quinicine and 4-[3-(6-butyl 4-quinolyl)propyl] piperidine was obtained, the fumarate of which melts at 140° C.

M.N.R. spectrum: —$CH_2$—N 2 to 3 ppm; —$CH_2$—$CH_2$ 0.5 to 1.6 ppm.

EXAMPLE 7

4(R)-[3-(6-methoxy 4-quinolyl)propyl]3(S)-vinyl piperidine 0.31 Grams of potassium hydroxide was added to a suspension of 1.1 g of 1-(6-methoxy 4-quinolyl)-3-[3(S)-vinyl-4(R)-piperidyl]-1-propanone dihydrochloride in 3.5 ml of diethylene glycol and 0.18 ml of an 85% aqueous solution of hydrazine hydrate. The mixture was heated slowly up to 150° C., then cooled to 100° C. and 0.47 g of potassium hydroxide were added. The reaction mixture was heated up to 150° C. and this temperature was maintained for five hours.

After cooling the reaction mixture was treated with 15 ml of water. The oil which salted out was extracted by ethyl acetate. The organic phase was decanted, washed, dried on magnesium sulphate and then evaporated. The crude oil obtained was fixed on a column containing 45 g of silica and then eluted with a 90/10 mixture of chloroform-diethylamine.

The purified product thus isolated was dissolved in acetone and transformed into its hydrochloride by adding a solution of hydrochloric acid in ether. 0.24 Grams of 4(R)-[3-(6-methoxy 4-quinolyl)propyl]3(S)-vinyl piperidine hydrochloride were obtained. This product melts at 151° C.

The starting ketone was prepared as follows:

20 Ml of distilled water were added to 2.1 g of 1-(6-methoxy 4-quinolyl)-3-[3(R)-vinyl 4(R)-piperidyl]-1-propanone (quinicine) and the pH was brought to 3.5 by adding a 1 N solution of sulfuric acid. The mixture was introduced in a 225 ml autoclave made of stainless steel and heated for 48 hours at 140° C. The solution was then made alkaline by adding a 2 N solution of sodium hydroxide and extracted with ether. The ethereal extract was washed with water, dried over anhydrous sodium sulfate and evaporated to dryness.

The residue obtained (1.7 g) was dissolved in a small amount of a 9/1 toluene-diethylamine mixture and fixed on a column containing 500 g of silica. It was then eluted with a 9/1 toluene-diethylamine mixture, under a pressure of 4 bars. 0.51 Grams of the starting product (quinicine) and 1.08 g of 1-(6-methoxy 4-quinolyl)-3-[3(S)-vinyl 4(R)-piperidyl]-1-propanone were thus isolated. The latter compound was dissolved in methanol and converted into its hydrochloride by adding an 8 N solution of hydrochloric acid in methanol.

EXAMPLE 8

4(R)-[3-(6-methoxy 4-quinolyl)propyl]3(S)-vinyl piperidine 2.1 Grams of 4(R)-[3-(6-methoxy 4-quinolyl)propyl]3-(R)-vinyl piperidine were dissolved in 20 ml of distilled water and the pH was adjusted to 2 by adding a 5 N solution of sulfuric acid. The mixture was introduced into a 225 ml stainless steel autoclave and heated for 48 hours at 140° C. Then the solution was made alkaline by adding a 2 N solution of sodium hydroxide and extracted with ether. The ethereal extract was washed with water, dried over anhyrous sodium sulfate and evaporated to dryness. The residue obtained (1.9 g) was dissolved in a little 9/1 toluene-diethylamine mixture and fixed on a column containing 500 g of silica. By eluting with a 9/1 toluene-diethylamine mixture under a pressure of 4 bars, 0.71 g of the starting product and 0.68 g of 4(R)-[3-(6 methoxy 4-quinolyl)propyl]3(S)-vinyl piperidine were isolated in the form of an oil.

The latter compound was dissolved in methanol and converted into its hydrochloride by adding a solution of hydrochloric acid in methanol.

Characteristics of 4(R)-[3-(6-methoxy 4-quinolyl)propyl]3(S)-vinyl piperidine hydrochloride:

Melting point: 151° C., Rotatory power (measured in water at 25° C.: $[\alpha]_D^{25} = -31°$.

N.M.R. spectrum (solvent: deuterochloroform; reference: tetramethylsilane):

The chemical shifts $\delta$ of the hydrogen atoms numbered 10, 11 and 11' in the formula (X) hereinafter are:

$\delta_{10} = 5.4$ ppm $\delta_{11, 11'} = 5$ ppm

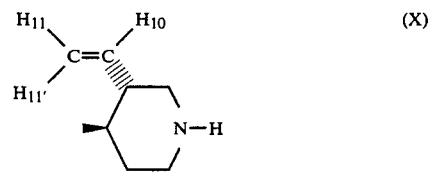
(X)

EXAMPLE 9

4(R)-[3-(6-methoxy 4-quinolyl)propyl]3(S)-ethyl piperidine

A well-stirred suspension containing 2 g of 10% palladized carbon and 6.8 g of 4(R)-[3-(6-methoxy 4-quinolyl)-propyl]3-(S)-vinyl piperidine monohydrochloride in solution in 100 ml of absolute ethanol was maintained at ambient temperature under a pressure of hydrogen corresponding to an excess pressure of 50 mm of water relative to atomspheric pressure, until the absorption of hydrogen ceased.

The palladized carbon was then separated by filtration and the alcoholic solution was concentrated. The residue was then dissolved in 50 ml of water and the solution was brought to pH 10 by adding a solution of sodium hydroxide.

The oil which salted out was extracted with chloroform and the extract was washed with water, then dried over magnesium sulfate. After evaporation of chloroform, the residual oil (5.6 g) was converted into fumarate by dissolution in ethanol and addition of 2.1 g of fumaric acid.

5.5 g of the acid fumarate of 4(R)-[3-(6-methoxy 4-quinolyl)propyl]3(S)-ethyl piperidine are obtained. This compound melts at 180° C.

Analysis for $C_{20}H_{28}N_2O$, $C_4H_4O_4$: Calculated: % N=6.54; Found: % N=6.47.

EXAMPLE 10

4(R)-[3-(4-quinolyl)propyl]3(S)-vinyl piperidine

By operating as in Example 8, but replacing the 2.1 g of 4(R)-[3-(6-methoxy 4-quinolyl)propyl]3(R)-vinyl piperidine with 1.3 g of 4(R)-[3-(4-quinolyl)propyl]3(R)-vinyl piperidine, 0.8 g of 4(R)-[3-(4-quinolyl)-propyl]3(S)-vinyl piperidine are obtained in the form of an oil.

Characteristics of 4(R)-[3-(4-quinolyl)propyl]3(S)-vinyl piperidine:

N.M.R. spectrum:

The chemical shifts δ of the hydrogen atoms numbered 10, 11 and 11' in formula (X) are:

$\delta_{10} = 5.4$ ppm $\delta_{11,11'} = 5.05$ ppm

Pharmacological Properties (1) Action of the Products on the Uptake of Serotonine: by synaptosomes It is known that antidepressant products known at present have the property of inhibiting the uptake of cerebral monoamines. The antidepressant activity of the products according to the present invention has therefore been shown, in vitro, by means of the test for inhibiting the uptake of cerebral monoamines (serotonine in particular) by synaptosomes of the rat's brain according to Kannengiesser and Coll.'s, Biochem. Pharmacol., 22, 73, 1973, which is relied on herein and the disclosure incorporated by reference.

The results, expressed by a 50% inhibiting dose $I_{50}$ which represents the product does in micromoles per liter reducing the uptake of serotonine by 50%, are compiled in the following Table 1.

TABLE 1

| Product | $I_{50}$ (μM/l) |
|---|---|
| Ex. 1 | 0.004 |
| Ex. 2 | 0.035 |
| Ex. 3 | 0.008 |

It can be seen from Table 1 that the products according to the present invention are strong agents for inhibiting the uptake of serotonine.

(2) Potentialing Effect of 5-HTP:

The effectiveness of the compounds of the present invention in blocking the uptake of serotonine has also been shown in the potentiation test of 5-hydroxytryptophan (5-HTP). The products of the present invention have the interesting property of potentiating (i.e. reinforcing) to a very high degree the effects of 5-HTP, the precursor of serotonine. This property has been shown in vivo in $CD_1$ (Charles River) male mice by means of the technique described hereinafter.

It is known that the administration of 5-HTP parenterally in mice causes, with large doses, a characteristic behavior, i.e. quivering, torsions of the trunk, displacement of the rear legs, shaking of the head and increased general motility. To show a potentiating power with respect to 5-HTP, the present inventors have therefore used to advantage one of the characteristic properties of the precursor of serotonine, i.e. quivering. The procedure used is inspired by that of C. Gouret, J. Pharmacol. (Paris), 5, 453, 1975, which is relied on herein and the disclosure incorporated by reference. Groups of 8 male mice were used. The chronological order of the test was as follows for the groups treated with both 5-HTP and the products according to the invention.

At time t=0, 150 mg/kg of 5-HTP were injected intraperitoneally (I.P.) in the form of a 9% aqueous solution of NaCl.

At time t=30 min., the product to the tested was injected subcutaneously (S.C.) in the form of a 9% aqueous solution of NaCl.

At time t=75 min., the quivering in each animal was measured using the following scale:

0=no quivering
1=quivering of average intensity
2=intense quivering

The chronological order was the same for the "control 5-HTP" and "control product" groups except that, in the first case, a 9% aqueous solution of NaCl was injected in the S.C. manner instead of the product solution and, in the second case, a 9% aqueous solution of NaCl was injected in the I.P. manner instead of the 5-HTP solution. The "control product" groups received the same doses of the tested product as the groups treated with both 5-HTP and the product in order to discover any possible effect inherent in the product.

The number of points for each group was totalled and the average indication of quivering was determined. On this basis an ED 50 was defined, for each product tested, which is the product dose in mg/kg for which 50% of the maximum possible effect, i.e. an average indication of quivering equal to 1, was obtained.

The results obtained are compiled in the following Table 2.

TABLE 2

| 5-HTP Dose mg/kg I.P. | Product Tested | ED 50 mg/kg S.C. |
|---|---|---|
| 150 | Example 1 | 14 |
| 150 | Example 2 | 12 |

With a dose of 25 mg/kg, the products of Examples 1 and 2 did not have any inherent effect (i.e. no effect in the absence of 5-HTP). The compounds of the present invention are therefore strong potentializers of 5-HTP. These activities are consistent with the remarkable effect of inhibiting the uptake of serotonine as observed on the synaptosomes of rats.

(3) Action of the Products on the Uptake of Serotonine and on the Release of Serotonine by platelets It is known that the uptake of serotonine by the blood platelets is a good model or indication of the uptake of this amine by neurons [see J. TUOMISTO, J. Pharm., Pharmac., 26 92 (1974)]. When it is applied to the investigation of medicaments, a method which brings into play the blood platelets presents great interest because it makes it possible to use human cells, which enables the method to give a good anticipation of the effect of the products on human beings.

The capacity of the products for inhibiting the uptake of serotonine or for causing its release has been shown on human blood platelets according to J. L. DAVID et al. "Platelets Function and Thrombosis, a Review of Methods" p. 335 (Plenum Press, London, 1972).

(a) Inhibition of the uptake of serotonine

The results are expressed by a 50% inhibiting dose $I_{50}$, which represents the product dose in micromoles per liter reducing the uptake of serotonine by 50%.

(b) Release of serotonine

The action of the products on the release of serotonine has been tested at two concentrations: $5 \times 10^{-6}$ mole per liter and $5 \times 10^{-5}$ mole per liter.

The results obtained are expressed by a percentage of increase of the release of serotonine in comparison with the results obtained with the controls.

The results obtained are compiled in the following Table 3. In this table are also given for comparison the results obtained with two reference products (imipramine and p-chloro amphetamine).

TABLE 3

| Product | Inhibition of the Uptake of serotonine $I_{50}$ (μM/l) | Percentage of increase of the release of serotonine | |
|---|---|---|---|
| | | Concentration of the product $5 \times 10^{-6}$ mole per liter | Concentration of the product $5 \times 10^{-5}$ mole per liter |
| Compound of Example 7 | 1 | 40 | 78 |
| Compound of Example 9 | 0.1 | 30 | 69 |
| Compound of Example 1 | 0.01 | 7 | 32 |
| Compound of Example 3 | 0.01 | 34 | 67 |
| Imipramine | 0.4 | 3 | 13 |
| p-Chloro amphetamine | 12 | 6 | 51 |

It can be seen from Table 3 that the compounds of Examples 7 and 9 are much less effective than their epimers as inhibitors of serotonine (the compound of Example 7 is one hundred (100) times less effective than its epimer, the compound of Example 1, and the compound of Example 9 is at least ten (10) times less effective than its epimer, the compound of Example 3). The compounds of Examples 7, 9 and 3 are powerful agents for the release of serotonine. They are even more effective than p-chloro amphetamine.

(4) Antiarythmic Activity

The antiarythmic activity of the compounds of the present invention has been shown by means of the aconitine test in rats. The method is based on the time necessary for the appearance of the ventricular arrhythmia caused by aconitine which is slowly perfused in rats. An antiarythmic product retards the appearance of arrhythmia and the appearance delay is proportional to the activity of the product.

Groups of 5 male rats were used. The rats were invidually anaesthetized (10% urethane: 1 g/kg intraperitoneally) to make it possible to effect a catheterization of the penis vein. The electrocardiogram was recorded. At time $t = 0$ the product to be tested was injected in the form of an aqueous solution at the rate of 2.5 ml. of solution per kg, in 30 seconds. At time $t = 90$ seconds, i.e. one minute after the end of injection, aconitine was perfused at the rate of 20 μg per minute until the appearance of supra-ventricular extra systoles. The perfusion time of aconitine was noted.

The results are expressed by an ED 50, which is the product dose in mg/kg increasing by 50% the perfusion time of aconitine in comparison with the perfusion time of the control animals.

The results obtained are compiled in the following Table 4 in which are given the activity (ED 50), the toxicity (LD 50) and the therapeutic index LD 50/ED 50.

TABLE 4

| Product | $LD_{50}$ I.V. mg/kg | $ED_{50}$ I.V. mg/kg | LD 50 / ED 50 |
|---|---|---|---|
| Example 1 | 30 | 2 | 15 |
| Example 2 | 30 | 12 | 2.5 |
| Example 3 | 21 | 0.7 | 30 |
| Example 4 | 42 | 15 | 2.8 |
| Example 5 | 22 | 2.3 | 9.6 |
| Quinidine | 70 | 7.5 | 9.3 |
| Disopyramide | 26 | 4 | 6.5 |

It is seen from the foregoing that the products of the invention are strong antiarythmic agents. Particularly the products of Examples 1, 3 and 5 not only are more effective than the reference products (quinidine and disopyramide) but also have a therapeutic index higher than that of quinidine and disopyramide.

(5) Potentiation of Sleep Induced by Serotonine:

The role of the cerebral serotonine in sleep is a well-known fact as reported by M. Jouvet and Coll., C. R. Acad. Sc. PARIS, 1967, 264, 360. The administration of serotonine to adult animals does not make it possible to observe the hypnogenic effects of this neurotransmitter because serotonine does not cross the hematoencephalic barrier. However, chickens do not have such a barrier and it is therefore possible to inject serotonine into chickens intravenously and to observe the central effects of serotonine.

Groups of 12 chickens were used, to which were administered intravenously serotonine at a dosage level of 0.1 mg/kg. It was noted that under these conditions 25% of the chickens were sent to sleep. When serotonine at a dosage level of 0.1 mg/kg, and a product of the invention, with a variable dosage simultaneously administered intravenously, it was noted that far more than 25% of the chickens were sent to sleep. For example, when the product of Example 1 was administered at a dosage level of 3 mg/kg, it was noted that 60% of the chickens were sent to sleep.

The products of the present invention potentiate therefore the hypnogenic effects of serotonine.

(6) Vascular Action:

The potentiation of the vascular effects of serotonine is shown according to the procedure of J. J. Loux, Arch. Int. Pharmacodyn. Therap. 1970, 183, 98, as modified by B. B. Vargaftig, Eur. J. Pharmacol. 1974, 25, 216, which are relied on herein and the disclosures incorporated by reference. The modified method consists in injecting into the carotid of an anaesthetized dog increasing and cumulated doses of serotonine. From 0.20 μg/kg upwards, an increase of the total volume of sinus was observed, which revealed a vasoconstriction of the nasal mucous membrane. This increase was measured by connecting the nasal sinus, hermetically isolated from outside, with a pressure gauge.

The products of the present invention did not show any inherent vasoconstrictive effect in this test, but did strongly potentiate the effect of serotonine. For example, the product of Example 1, at a dosage rate of 1 μg/kg administered intravenously potentiated the vascular effect of 0.05 μg/kg of serotonine in that the pressure decrease measured by the gauge was twice greater.

This activity of the products of the invention may be used for the treatment of migraines as described by F. Sicuteri and Coll., Psychopharmacologia, 1973, 29, 327, which is relied on herein and the disclosure incorporated by reference.

(7) Anxiolytic Properties

The anxiolytic activity of the compounds of formula (I) was demonstrated in vitro using inhibition of specific $^3$H-diazepam binding to rat brain membranes according to the method of Möhler, H. et al., Life Sci., 20, 1977, page 2101. The entire disclosure of Möhler et al. is relied upon in this connection and is incorporated herein by reference.

The results listed in Table 5 below show that these products are characterized by a strong $^3$H-diazepam displacement potency.

TABLE 5

| Inhibition of Specific $^3$H-Diazepam Binding To Rat Brain Membranes | |
|---|---|
| PRODUCTS | $K_i$ (in μM) |
| Example 1 | 5.5 |
| Example 2 | 2.5 |
| Example 3 | 4.5 |
| Example 4 | 3.5 |
| Example 5 | 8 |
| Example 7 | 5 |
| Example 9 | 5 |
| Imipramine | inactive |

The effectiveness of the compounds of formula (I) in the test of Möhler does not correlate with an effectiveness in behavioral screening tests such as antagonism of foot shock-induced fighting in mice wherein benzodiazepines are active (cf. Tedeschi, R. E. et al., J. Pharmacol., 125 (1959), 28.). This discrepancy confers to the products of the invention an entirely new spectrum of activity that is anxiolytic effectiveness without sedative properties.

Toxicological Properties

The acute toxicities and symptomatologies of the compounds according to the present invention have been determined on $CD_1$ (Charles River) male mice by I.V. and oral methods. The $LD_{50}$'s were calculated, after 3 days of observation, by the cumulative method of J. J. Reed & H. Muench, Amer. J. Hyg., 27, 493, 1938, which is relied on herein and the disclosure incorporated by reference.

The symptomatologies observed with the toxic and subtoxic doses were analogous for the products and for the two methods of administration used. They consisted principally of catatonia of the tail, quivering, respiratory depression and clonic convulsions.

The $LD_{50}$'s obtained are compiled in the following table 6.

TABLE 6

| | ACUTE TOXICITY IN MICE LD mg/kg | |
|---|---|---|
| PRODUCTS | I.V. | P.O. |
| Example 1 | 30 | 600 |
| Example 2 | 30 | 525 |
| Example 3 | 21 | 600 |
| Example 4 | 42 | 600 |
| Example 5 | 22 | 600 |
| Example 7 | — | 225 |
| Example 9 | — | 200 |

The compounds therefore behave like substances which exhibit relatively little or no toxicity to mice.

Therapeutic Applications

The compounds of the invention and their pharmaceutically acceptable salts may be used in mammalian, including but not limited to human, therapy in the form of pills, tablets, lozenges, troches, capsules, suppositories, injectable or ingestable solutions and the like in the treatment of pathological conditions in mammals caused by disturbances in the functioning of the serotoninergical systems, in particular as regards the various phycological difficulties involving depression, as medicines for regulating sleep, as antiarythmic medicaments and as regulators of the vasoconstriction of blood vessels.

The products of formula I are useful not only in the symptomatic relief of tension but also in anxiety states resulting from stressful circumstances or whenever somatic complaints are concomitant of emotional factors. They are useful in psychoneurotic states manifested not only by depressive symptoms but also by tension, anxiety, apprehension or agitation.

Unlike benzodizepines which are well known as anxiolytics and sedatives, the compounds of formula I and their pharmaceutically acceptable salts are devoid of sedative effects. They act as psychic stimulants.

The mammals which may be treated, within the contemplation, include humans, as well as laboratory animals, for example, dogs, cats, guinea pigs, mice and rats.

For the foregoing purposes the compounds described above may be administered in a therapeutically effective amount, such as to a mammal, orally, parenterally, intravenously or subcutaneously.

For purposes of injection the compounds described above can be prepared in the form of solutions, suspensions or emulsions in vehicles conventionally employed for this purpose.

The dosage depends on the effects sought and on the manner of administration. Orally, for instance, it may range from 5 to 250 mg of active substance a day, each unit dose ranging from 1 to 50 mg.

Appropriate pharmaceutically acceptable carriers, diluents and adjuvants may be and together with the compounds described herein in order to prepare the desired compositions for use in the treatment of pathological conditions in mammals.

The pharmaceutical compositions of this invention will contain the active compound together with a solid or liquid pharmaceutically acceptable nontoxic carrier. Such pharmaceutical carriers can be sterile liquids, such as water and oils, including those of petroleum, animal, vegetable or snythetic origin, such as peanut oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the host. While intravenous injection is a very effective form of administration, other modes can be employed.

What is claimed is:

1. A method for the treatment of a mammal afflicted with a disturbance in the functioning of serotoninergical systems which comprises administering to said mammal a therapeutically effective amount of a compound of the formula

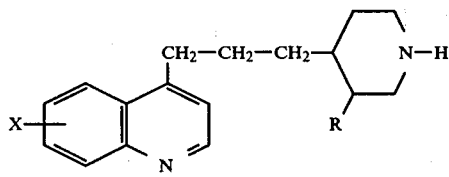

(I)

wherein R is hydrogen, alkyl having 1 to 4 carbon atoms or alkenyl having 2 to 4 carbon atoms;

X is hydrogen or halogen, alkyl, alkoxy or alkylthio having 1 to 4 carbon atoms, trifluoromethyl, nitro, hydroxy, amino or amino substituted by one or two alkyl groups having 1 to 4 carbon atoms, by acyl having 1 to 4 carbon atoms or by alkylsulphonyl group having 1 to 4 carbon atoms, or a pharmaceutically acceptable salt thereof in a pharmaceutically acceptable carrier therefor.

2. A method as defined in claim 1 wherein said compound corresponds to formula (I) wherein R is hydrogen, ethyl or vinyl and X is hydrogen or methoxy in position 6.

3. The method as defined in claim 1 wherein said compound is 4(R)-[3-(6-methoxy 4-quinolyl)-propyl]3(R)-vinyl piperidine.

4. The method as defined in claim 1 wherein said compound is 4(R)-[3-(3-quinolyl)propyl]3(R)-vinyl piperidine.

5. The method as defined in claim 1 wherein said compound is 4(R)-[3-(6-methoxy-4-quinolyl)-propyl]3(R)-ethyl piperidine.

6. The method as defined in claim 1 wherein said compound is 4-[3-(4-quinolyl)propyl]piperidine.

7. The method as defined in claim 1 wherein said compound is 4(R)-[3-(4-quinolyl)propyl]3(R)-ethyl piperidine.

8. The method as defined in claim 1 wherein said compound is 4-[3-(6-butyl 4-quinolyl)propyl]piperidine.

9. The method of claim 1 wherein said compound is 4(R)-[3-(6-methoxy 4-quinolyl)propyl]3(S)-vinyl piperidine.

10. The method of claim 1 wherein said compound is 4(R)-[3-(6-methoxy 4-quinolyl)propyl]3(S)-ethyl piperidine.

11. The method of claim 1 wherein said compound is 4(R)-[3-(4-quinolyl)propyl]3(S)-vinyl piperidine.

12. The method of claim 1 for the treatment of depression.

13. A medicament for the treatment of pathological states of a mammal caused by a disturbance in the functioning of serotoninergical systems containing as active ingredient a pharmaceutically effective amount of 4(R)-[3-(6-methoxy 4-quinolyl)-propyl]3(S)-vinyl piperidine or a pharmaceutically acceptable salt thereof, in a pharmaceutically acceptable carrier.

14. A medicament for the treatment of pathological states of a mammal caused by a disturbance in the functioning of serotoninergical systems containing as active ingredient a pharmaceutically effective amount of 4(R)-[3-(6-methoxy 4-quinolyl)-propyl]3(S)-ethyl piperidine or a pharmaceutically acceptable salt thereof, in a pharmaceutically acceptable carrier.

15. A medicament for the treatment of pathological states of a mammal caused by a disturbance in the functioning of serotoninergical systems containing as active ingredient a pharmaceutically effective amount of 4(R)-[3-(4-quinolyl)propyl]3-(S)-vinyl piperidine or a pharmaceutically acceptable salt thereof, in a pharmaceutically acceptable carrier.

* * * * *